United States Patent [19]

Buchmüller et al.

[11] Patent Number: 4,829,783
[45] Date of Patent: May 16, 1989

[54] DEVICE FOR THE CONTROLLED FREEZING OF VISCOUS LIQUIDS

[75] Inventors: Jürgen Buchmüller, Krefeld; Günther Weyermanns, Huckelhoven, both of Fed. Rep. of Germany

[73] Assignee: Messer Griesheim GmbH, Fed. Rep. of Germany

[21] Appl. No.: 176,928

[22] Filed: Apr. 4, 1988

[30] Foreign Application Priority Data

Apr. 2, 1987 [DE] Fed. Rep. of Germany ....... 3711169

[51] Int. Cl.⁴ .............................................. F25D 17/02
[52] U.S. Cl. ......................................... 62/373; 62/78
[58] Field of Search ................... 62/64, 78, 55, 50, 49, 62/373

[56] References Cited

U.S. PATENT DOCUMENTS

| | | | |
|---|---|---|---|
| 3,228,838 | 1/1966 | Rinfret et al. | 62/78 |
| 3,729,946 | 5/1973 | Massey | 62/55 |
| 3,777,988 | 12/1973 | Thompson | 62/374 |
| 4,607,489 | 8/1986 | Krongold | 62/49 |

Primary Examiner—Ronald C. Capossela
Attorney, Agent, or Firm—Connolly & Hutz

[57] ABSTRACT

A device for the controlled deep freezing of viscous liquids by means of a low boiling liquified gas is used for producing drops from the liquid, which are frozen to pellets in a liquid nitrogen bath. The device includes a container arranged above the bath to hold the liquid to be frozen. The bottom of the container consists of two drip plates which can be moved in relation to each other and are provided with bores.

7 Claims, 2 Drawing Sheets

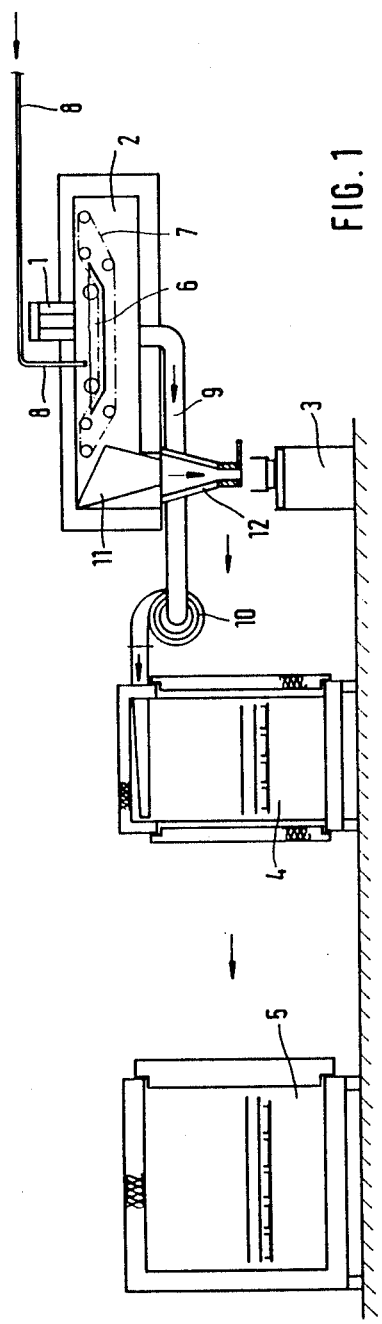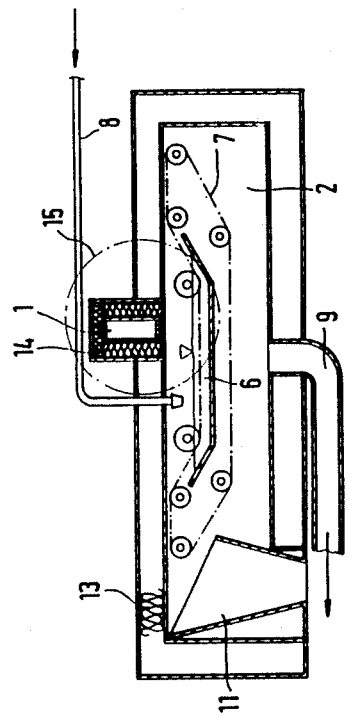

DEVICE FOR THE CONTROLLED FREEZING OF VISCOUS LIQUIDS

BACKGROUND OF INVENTION

Liquids can be preserved when they are frozen in bags or bottles made of plastic material and, if necessary, are vacuum dried. When these are sensitive liquids with organic components, freezing must take place as quickly and uniformly as possible, in other words, controlled to prevent cold damage. This applies, in particular, when these organic components are living cells, for example, bacteria suspensions. When freezing is uncontrolled, the wall of the cell and cellular tissue may be destroyed as a result of a severe ice crystal formation.

Such a bacteria suspension consists, for example, of 95% water and 5% bacteria. With uncontrolled freezing, the survival rate of these cells may drop to an unacceptable low degree. But liquids with other organic components, for example, albumen solutions, vitamin solutions and vaccines may be damaged by uncontrolled freezing. A proven method of freezing such liquids for the purpose of preservation is to conduct freezing by means of a low boiling liquified gas, as a rule nitrogen. With liquid nitrogen as refrigerant, the liquid, for example, in bags or ampules can be cooled very quickly to the desired freezing temperature so that there is, for example, little time for an extensive ice crystal formation. But some time is needed to freeze such a liquid specimen from the outside to the inside so that to some degree inevitable cold damage and concentration of components in the core of the liquid occur.

British Pat. No. 1,376,972 discloses a device which provides for a very gentle freezing of such a liquid, namely, liquid egg. With this device, drops of liquid egg are produced, led into a bath consisting of a low-boiling liquified gas from which they are removed in the form of frozen pellets. The liquid can be deep frozen extremely fast to the target temperature because the drop has a small volume. This is still enhanced by the direct heat exchange between liquid and cooling medium since separating intermediate walls between cooling medium and the liquid to be deep frozen are eliminated. The spherical shape of the drops results, moreover, in a ratio of liquid surface to volume which is optimum for uniform freezing. The drops are produced with a peristaltic pump by a periodic compression of flexible tubes filled with the liquid to be frozen so that drops of the liquid are expelled from the flexible tube and through nozzles are led into the refrigeration bath.

This type of drops production is cumbersome. The peristaltic pump is a relatively complicated and trouble-prone machine which requires a constant monitoring. Since it is placed in the immediate vicinity of the cooling medium bath, there is the risk that the nozzles ice up. When a certain pellet diameter must be absolutely maintained, there are also problems since with the known device only pellets having a somewhat same diameter can be produced. A controlled freezing or sensitive liquid requires, however, drops and pellets having a uniform size because identical and, therefore, controlled freezing conditions can only be realized with such uniform sizes. The known device also has only limited possibilities, for example, for varying the size of the drops via the throughput. But when different liquids having a different viscosity are to be frozen to pellets, it is often desirable that a certain pellet size is associated with a certain liquid.

SUMMARY OF INVENTION

The invention is based on the objective of providing a device for the controlled deep freezing of viscous liquids to frozen pellets which makes the production possible of pellets having almost the same diameters, the variation of the pellet size and is simple, rugged and substantially maintenance-free.

The condition that the liquid to be frozen must be viscous only means that drops having a defined size can be produced from the liquid. Liquids with a very broad viscosity range are, therefore, suitable for the device of the invention; only very low viscosity liquids are not suitable. It is important that the drops, while falling into the cooling medium bath, have sufficient time to assume the spherical shape. But the drops also may not enter the bath, for example, consisting of liquid nitrogen at too high a speed since the spherical shape of the drops might then be impaired. In addition to the size of the drops, their falling path into the liquid nitrogen bath, in other words, their drop height is decisive for an optimum freezing of the liquid. The appropriate optimum drop height can be easily determined for each liquid by simple tests.

Another important criterion for an optimally controlled freezing process is the dwell time in the bath consisting of liquid cooling medium. The dwell time can be simply regulated by means of a conveyor belt running through the bath and known per se, which has baffles to transport the liquid drops frozen to pellets.

THE DRAWINGS

FIG. 1 shows a complete deep freezing installation and subsequent vacuum drying;

FIG. 2 shows the freezing and drop formation device of FIG. 1 on an enlarged scale;

DETAILED DESCRIPTION

Figure 3:
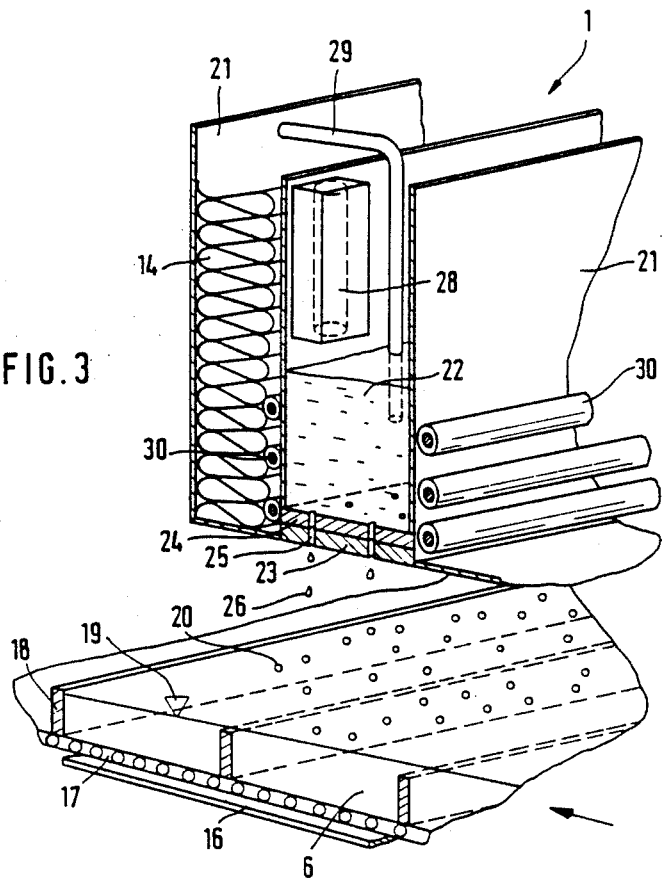
FIG. 3 shows a section of FIG. 2.

The essential parts of the installation shown in FIG. 1 consists of the drop formation device 1, the freezing unit 2, the catching device 3, a freezer 4 and a vacuum drier 5. The liquid to be frozen in present in the drop formation device 1 and drips into a liquid nitrogen bath 6 present in the freezing unit 2. A conveyor belt 7 runs through the bath 6 at an adjustable rotational speed. Liquid nitrogen arrives through line 8 in the freezing unit 2 to replace the evaporated nitrogen. The evaporated nitrogen is withdrawn from the freezing unit 2 through the pipe 9 by means of the fan 10 and serves to keep the freezer 4 used as intermediate storage at a suitable temperature, for example, −60° C. The flow and travel directions are indicated by arrows without reference numbers.

The liquid dripping from the drop formation device 1, according to the invention, into the liquid nitrogen bath 6 freezes there to pellets and, after a predetermined dwell time, is carried away from the bath 6 by the conveyor belt 7. The pellets drop through the funnels 11 and 12 into the catching device 3 where they are caught in basins. The basins filled with pellets are placed in the freezer 4 for intermediate storage. They are then placed in the vacuum drier 5 from which the finished product can be removed.

The pellets falling from the funnel 12 can of course also be directly caught in bags and stored in a freezer, for example, at −40° C.

FIG. 2 shows the freezing unit 2 somewhat enlarged. The whole freezing unit 2 is surrounded by an insulation 13 to diminish the cold losses. The drop formation device 1 also has an insulation 14 to keep the liquid to be deep frozen at an as constant as possible temperature. The detail characterized by the dash-dot circle 15 is shown in FIG. 3 in an enlarged perspective drawing.

FIG. 3 shows a part of the trough 16 which contains the liquid nitrogen bath 6. The conveyor belt 17 slides through the bath 6 and is provided with baffles 18. The surface 19 of the liquid nitrogen is higher than the baffles 18. The pellets 20 to be deep frozen are present between the baffles 18 and are deep frozen to a core temperature of −40° C.

The drop formation device 1 is found above the liquid nitrogen bath 6. This device essentially consists of a container 21 which holds the liquid 22 to be frozen. The bottom of the container 21 consists of the drip plates 23 and 24. The drip plates 23, 24 are provided with bores 25 and have more or less open area by moving one drip plate, preferably, the bottom drip plate 23 so that variable throttling positions are produced which control the flow rate of the liquid 22 to be frozen in such a way that the drop sequence is determined. The drip plates 23, 24 are, preferably, exchangeable so that drip plates with different size bores 25 can be used depending on the viscosity of the liquid 22 to be frozen and on the desired drop size.

Figure 4:
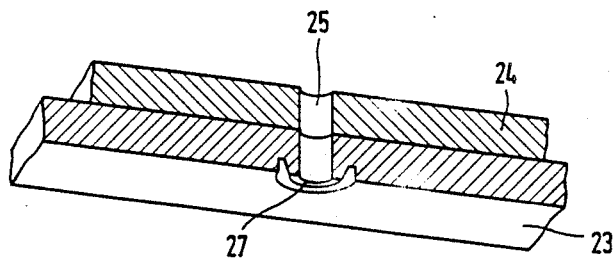
FIG. 4 shows a detail of the drop formation device.

FIG. 4, on an enlarged scale, shows a perspective drawing of parts of the drip plates 23 and 24 with a bore 25. Depending on the viscosity of the liquid to be frozen, the annular surface is either larger or smaller.

FIG. 3 also shows other devices which make sure that the drops 26 have a constant size. The proximity switch 28, for example, keeps the level of the liquid 22 constant and controls the appropriate liquid delivery through the line 29 so that the pressure of the liquid 22 in front of the bores 25 is constant. Instead of the proximity switch 28, also other means used for this purpose may be employed. The container 21 is, moreover, surrounded by a heating tape 30 which keeps the temperature of the liquid 22 constant.

This is important since the viscosity of the liquid is highly dependent on the temperature, the viscosity in turn is codecisive for the viscosity of the drops 26 and a freezing up of the bores 25 is prevented at the same time.

The device according to the invention can, therefore, be used to produce drops having a constant and reproducible size from a given liquid. A controlled deep freezing then only still requires that the drops penetrate the nitrogen bath in spherical shape and that the dwell time in the nitrogen bath is exactly fixed. The dwell time is exclusively determined by the rotational speed of the conveyor belt 17. The baffles 18 make sure that all drops 26 immediately after they dip into the liquid nitrogen are moved through the bath 6 for a predetermined time whereby they are frozen to pellets having the desired core temperature. In order to attain the desired spherical shape which makes an extremely uniform deep freezing possible, the fall height of the drops 26 must be adapted to the appropriate liquid. Very viscous liquids require longer falling paths since they are slower to assume the spherical shape. The best fall height can be quickly found by means of a few tests since the shape of the pellet immediately demonstrates whether the fall height is optimum.

The device according to the invention is suitable for all liquids having a viscosity which allows for a controlled and reproducible drop formation. Bacteria suspensions with solids fractions ranging from 8 to 16 wt. % were successfully frozen, for example. These bacteria suspensions had viscosities ranging from 0.001 to 12.5 $Ns/m^2$ and surface tensions from 0.05 to 0.08 $Ns/m$. Depending on the viscosity of the bacteria suspensions to be frozen, drip plates with different dimension bores were used. The smallest bore diameter was 0.7 mm, the largest bore diameter was 2 mm. The thickness of the drip plate facing the nitrogen bath also influences the size of the produced drops to some extent. But the height of the drop, in other words, the distance of the bottom drip plate from the level of the nitrogen bath has a much greater influence. In individual cases, for example, optimum drop heights ranging from 50 to 120 mm were determined. The diameter of the spherical pellet obtained in this way was between 2 and 5 mm. A certain bore diameter, a certain drop height and a certain sphere diameter must always be associated with a certain bacteria suspension.

SUMMARY

Viscous liquids, for example, bacteria suspensions or vaccines can be deep frozen in low-boiling liquified gases by producing drops from the liquid, which are frozen to pellets. For the production of pellets having substantially equal diameters, a container 21 is used which is arranged above the bath 6 consisting of liquified gas which is filled with the liquid 22 to be frozen. The bottom of the container consists of two drip plates 23, 24 provided with bores 25 which can have more or less open area so that a variable throttling position is produced which determines the flow rate of the liquid and, therefore, the sequence of the drops. Viscosity of the liquid and the diameter of the bore determine the drop size. The discharge edges of the bores are designed as release edges to make the size of the drops as uniform as possible (FIG. 3).

What is claimed is:

1. In a device for the controlled deep freezing of viscous liquids by means of a low-boiling liquified gas, which device is used for the production of drops from the liquid, which are frozen to pellets in a liquid nitrogen bath, the improvement being in that said device includes a liquid nitrogen bath, a container arranged above said bath to hold the liquid to be frozen, viscous liquid supply means communicating with said container, the bottom of said container consisting of two drip plates which can be moved in relation to each other, and said drip plates being provided with alignable bores.

2. Device according to claim 1, characterized in that the edges of said bores of said bottom drip plate facing the surface of said bath are designed as release edges.

3. Device according to claim 2, characterized by means for maintaining a constant liquid level in said container.

4. Device according to claim 3, characterized by a heating tape surrounding said container to maintain a constant temperature of said liquid.

5. Device according to claim 2, characterized by a heating tape surrounding said container to maintain a constant temperature of said liquid.

6. Device according to claim 1, characterized by a heating tape surrounding said container to maintain a constant temperature of said liquid.

7. Device according to claim 1, characterized by means for maintaining a constant liquid level in said container.

* * * * *